(12) United States Patent
Utzinger et al.

(10) Patent No.: US 6,766,184 B2
(45) Date of Patent: Jul. 20, 2004

(54) METHODS AND APPARATUS FOR DIAGNOSTIC MULTISPECTRAL DIGITAL IMAGING

(75) Inventors: Urs Utzinger, Tucson, AZ (US); Rebecca Richards-Kortum, Austin, TX (US); Calum MacAuldy, Cancouver (CA); Michele Follen, Houston, TX (US)

(73) Assignees: Board of Regents, The University of Texas System, Austin, TX (US); BC Cancer Agency, Vancouver (CA)

( * ) Notice: Subject to any disclaimer, the term of this patent is extended or adjusted under 35 U.S.C. 154(b) by 369 days.

(21) Appl. No.: 09/821,786

(22) Filed: Mar. 28, 2001

(65) Prior Publication Data

US 2002/0065468 A1 May 30, 2002

Related U.S. Application Data

(60) Provisional application No. 60/192,542, filed on Mar. 28, 2000.

(51) Int. Cl.$^7$ .................................................. A61B 5/05
(52) U.S. Cl. ....................... 600/407; 600/591; 600/425; 356/318; 356/417; 356/418
(58) Field of Search ................................ 600/407, 591, 600/478, 477, 476, 408, 409, 410, 424, 425, 426, 427, 437–471; 356/318, 417, 418, 416, 301, 310

(56) References Cited

U.S. PATENT DOCUMENTS

| 5,421,339 A | 6/1995 | Ramanujam et al. ........ 128/665 |
| 5,590,660 A | 1/1997 | MacAulay et al. ......... 128/664 |
| 5,647,368 A | 7/1997 | Zeng et al. ................. 128/665 |
| 5,769,792 A | 6/1998 | Palcic et al. ................. 600/477 |
| 5,920,399 A | * 7/1999 | Sandison et al. ........... 356/418 |
| 5,929,985 A | * 7/1999 | Sandison et al. ........... 356/318 |
| 5,984,861 A | 11/1999 | Crowley ....................... 600/175 |
| 6,343,228 B1 | 1/2002 | Qu .............................. 600/476 |
| 6,370,422 B1 | * 4/2002 | Richards-Kortum et al. ............. 600/478 |
| 6,504,943 B1 | * 1/2003 | Sweatt et al. ................ 356/310 |
| 6,571,118 B1 | * 5/2003 | Utzinger et al. ............. 600/476 |
| 6,593,101 B2 | * 7/2003 | Richards-Kortum et al. ..... 600/478 |

FOREIGN PATENT DOCUMENTS

| DE | 19626433 | 1/1998 |
| WO | WO 00/42912 | 7/2000 |
| WO | WO 01/72214 | 10/2001 |

OTHER PUBLICATIONS

Balas et al., "In vivo assessment of acetic acid–cervical tissue interaction using quantitative imaging of back–scattered light: its potential use for the in vivo cervical cancer detection grading and mapping," *Proceedings of the SPIE*, 3568:31–37, 1998.

(List continued on next page.)

*Primary Examiner*—Henry Bennett
*Assistant Examiner*—Fadi H. Dahbour
(74) *Attorney, Agent, or Firm*—Fulbright & Jaworski LLP

(57) ABSTRACT

Methods and apparatus for generating multispectral images of tissue. The multispectral images may be used as a diagnostic tool for conditions such as cervical cancer detection and diagnosis. Primary radiation is produced with an illumination source. The primary radiation is filtered to select a first wavelength and a first polarization. Tissue is illuminated with the filtered primary radiation to generate secondary radiation, which is filtered to select a second wavelength and a second polarization. The filtered secondary radiation is collected with a detector, and a plurality of multispectral images of the tissue is generated according to different combinations of first and second wavelengths and first and second polarization with an analysis unit in operable relation with the detector. Apparatus utilizing the invention include endoscopes and colposcopes.

25 Claims, 3 Drawing Sheets

OTHER PUBLICATIONS

Jichlinski et al., "Clinical evaluation of a method for detecting superficial surgical transitional cell carcinoma of the bladder by light–induced fluorescence of protoporphyrin IX following topical application of 5–aminolevulinic acid: preliminary results," *Lasers in Surgery & Medicine*, 20(4):402–408, 1997.

Lam et al., "Detection and localization of early lung cancer by imaging techniques," *Chest*, 103(1 Suppl):12S–14S, 1993.

Perelman et al., "Observation of Periodic Fine Structure in Reflectance from Biological Tissue,: A New Technique for Measuring Nuclear Size Distribution," *Physical Review Letters*, 80(3), 627–630, 1998.

Pogue et al., "Multi–wavelength digital colposcopy to aid early detection of cervical cancer," *Biomedical Optical Spectroscopy & Diagnostics/Therapeutic Laser Applications, TOPS*, 22(Joint Volume ):118–121, 1998.

Qu et al., "Correction of geometrical effects on fluorescence imaging of tissue," *Optics Communication*, 176:319–326, 2000.

Qu et al., "Optical processing of light induced autofluorescence for characterizationof tissue pathology," *Optics Letters*, 26:1268–1270, 2001.

Sokolov et al., "Reflectance spectroscopy with polarized light: is it sensitive to cellular and nuclear morphology," *Optics Express*, 5(13):302–317, 1999.

Sterenborg et al., "In vivo fluorescence spectroscopy and imaging of human skin tumors," *Dermatologic Surgery*, 21(9):821–822, 1995.

Svanberg et al., "Clinical multi–colour fluorescence imaging of malignant tumours–initial experience,"*Acta Radiologica*, 39(1):2–9, 1998.

Zangaro et al., "Rapid multiexcitation fluorescence spectroscopy system for in vivo tissue diagnosis," *Applied Optics*, 35(25):5211–5219, 1996.

\* cited by examiner

METHODS AND APPARATUS FOR DIAGNOSTIC MULTISPECTRAL DIGITAL IMAGING

This application claims priority to provisional patent application Ser. No. 60/192,542 filed Mar. 28, 2000, entitled, "Methods and Apparatus for Diagnostic Multispectral Digital Imaging" by Urs Utzinger, Rebecca Richards Kortum, Calum MacAuley, and Michele Follen. The entire text of the above-referenced disclosure is specifically incorporated by reference herein without disclaimer.

BACKGROUND OF THE INVENTION

1. Field of the Invention

The present invention relates generally to the fields of diagnostic imaging. More particularly, it concerns methods and apparatus for generating multispectral images that may be used to diagnose various conditions in various tissues. Even more particularly, it concerns methods and apparatus for generating multispectral digital images using fluorescence, reflectance, and polarized reflectance imaging techniques.

2. Description of Related Art

Over the last fifty years, Papanicolaou Smear ("Pap Smear") has become the cornerstone of efforts to reduce cervical cancer mortality. Pap Smear is effective because it identifies the latest stages of cervical cancer. Current estimates are that 60–70 million Pap Smears are done in the U.S. each year. Pap Smear has thus become a norm in the detection of cervical cancer. In spite of its broad acceptance in the medical community, studies indicate that Pap Smear screenings will fail to detect from 50%–80% of low grade cancerous lesions, and even 15%–30% of high grade cancerous lesions.

When conducting Pap Smear screenings, a gynecologist collects exfoliated cells from the surface of the cervix and places them on slides that are sent to cytologists for further examination. Cytologists then review the cells placed on the slides and look for abnormal cells. If abnormal cells are found, the Pap Smear is considered to be positive. If no abnormal cells are found, the Pap Smear is considered to be negative. It is also possible that Pap Smear slides cannot be properly evaluated by the cytologist because of technical problems associated with the Pap Smear collection process such inadequate cell count, improper slide fixation, etc.

In the early stages of cervical disease, abnormal cell exfoliation is slow and most abnormal cells are located below the surface or are trapped by a keratin barrier covering the cervical surface. In these circumstances, the Pap Smear screening process is a relatively insensitive indicator of cervical health due to inaccessibility of abnormal cells that are otherwise indicators of cancerous or pre-cancerous tissue. Human Papilloma Virus ("HPV") is the most common cause of keratin barriers to exfoliation. Further, it is commonly known that a significant portion of the U.S. population harbors this virus which therefore complicates the challenge of cervical cancer detection when using the Pap Smear as the principal screening procedure.

Because of a variety of problems associated with Pap Smear screening, it is well known that the Pap Smear procedure has both a high false negative, and a high false positive rate. Nevertheless, in spite of its cancer detection shortcomings, Pap Smear screening is generally recognized as a practical and economical procedure for the early detection of cervical cancer. While the Pap Smear process is designed for initial screening, colposcopy and related procedures are generally used to confirm Pap Smear abnormalities and to grade cancerous and potential cancerous lesions.

Since its introduction in 1925, colposcopy has acquired wide recognition as a follow-up clinical procedure for patients identified by Pap Smear screening as having possible cervical abnormalities. It is generally recognized that colposcopy is highly effective in evaluating patients with abnormal Pap Smears and has therefore become the standard of medical care in the Western world for this circumstance. It is estimated that approximately 4 million colposcopy examinations are currently performed in the U.S. each year. Its routine use, however, is time consuming and costly. Further, proper colposcopy examinations are limited by the expertise of the examiner.

Colposcopy is faced with its own set of challenges. It is a subjective assessment and the quality depends greatly on the expertise of the practitioner. It is time consuming with significant legal risks associated with false negative evaluations, and is therefore expensive. Certain types of computer-aided colposcopy, while capable of generating, storing and manipulating certain types of image data for the production of high-quality images, are currently unwieldy and expensive. Such colposcopes send signals to a remote computer through 5 to 7 meter long coaxial cables. As the colposcope is maneuvered to visualize the cervix, the wiring may become tangled with the patient or other equipment. Further, the remote location of the computer and video monitor prevents the patient from viewing the image as the examination is being conducted. Thus, these colposcopes provide an uncomfortable setting for the patient during examination. Further, the remote location of the video monitor also makes the viewing of the image difficult for the doctor while operating the colposcope.

Traditional colposcopes rely upon a single type of imaging—reflectance. However, reflectance data does not provide a complete picture of the state of tissue being examined. Further, the detector used for traditional colposcopy is most often the human eye. Therefore, accurate analysis of information obtained from the colposcope is highly dependent upon the skill of the operator in interpreting what is seen through the instrument. Although certain optical filters may be used to enhance contrast or to highlight certain types of tissue, the operator must still exhibit a relatively high level of skill to avoid false negative evaluations.

A need therefore exists in the area of cervical cancer screening and detection for apparatus and methods that may enhance or replace traditional colposcopy to allow for more accurate, real-time diagnosis. Specifically, a need exists for a technique that uses multispectral imaging techniques to provide high-resolution, two-dimensional images that may be used, for instance, to detect cervical pre-cancer.

SUMMARY OF THE INVENTION

In one respect, the invention is an apparatus for generating multispectral images of tissue. The apparatus includes an illumination source, a detector, an illumination filter, a detection filter, and an analysis unit. The illumination source is configured to illuminate the tissue with radiation. The detector is configured to collect radiation from the tissue. The illumination filter is in operative relation with the illumination source and is configured to select a first wavelength and a first polarization of radiation to be directed from the source to the tissue. As used herein, "wavelength" is to be interpreted broadly to include not only a single wavelength, but a range of wavelengths as well. Similarly, as used herein, "polarization" is to be interpreted broadly to include not only a single polarization orientation, but a range of polarizations as well. The detection filter is in operative relation with the detector and is configured to select a second wavelength and a second polarization of radiation to be directed from the tissue to the detector. The analysis unit is in operative relation with the detector and is configured to generate a plurality of multispectral images of the tissue according to different combinations of first and second wavelengths and first and second polarizations.

In other respects, the first and second wavelengths may be equal. The first and second polarizations may be equal. The apparatus may also include illumination optics and imaging optics. The illumination optics may be in operative relation with the illumination source and may be configured to direct radiation from the illumination source to the tissue. The imaging optics may be in operative relation with the tissue and may be configured to direct radiation from the tissue to the detector. The illumination optics may include a fiber bundle. The detection optics may include a fiber bundle. The illumination filter may be integral with the illumination source. The detection filter may be integral with the detector. The illumination source may include a tunable pulsed laser. The illumination source may include a pulsed flashlight. The detector may include a CCD camera. The illumination filter may include a bandpass filter, a filter wheel, or a tunable filter. The tunable filter may include an acousto-optical filter or a liquid crystal filter. The detection filter may include a bandpass filter, a filter wheel, or a tunable filter. The tunable filter may include an acousto-optical filter or a liquid crystal filter. The illumination and detection filters may be integral. The tissue may include a cervix. The plurality of multispectral images may include images of approximately the entire cervix. The plurality of multispectral images may include images of fluorescence, reflectance, polarized reflectance, or any combination thereof. The apparatus may be coupled to an endoscope. The apparatus may be coupled to a colposcope. The analysis unit may also be configured to generate a composite image of the tissue, the composite image incorporating one or more features of the plurality of multispectral images. The composite image may include information relating to the size of one or more lesions of the tissue.

In another respect, the invention is a method for generating multispectral images of tissue. Primary radiation is produced with an illumination source. The primary radiation is filtered to select a first wavelength and a first polarization. The tissue is illuminated with the filtered primary radiation to generate secondary radiation. The secondary radiation is filtered to select a second wavelength and a second polarization. The filtered secondary radiation is collected with a detector. A plurality of multispectral images of the tissue are generated according to different combinations of first and second wavelengths and first and second polarization with an analysis unit in operable relation with the detector.

In other respects, the method may also include generating a composite image of the tissue, the composite image incorporating one or more features of the plurality of multispectral images. The method may also include determining the size of one or more lesions using the composite image. The plurality of multispectral images may include images of fluorescence, reflectance, polarized reflectance, or any combination thereof.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present disclosure describes apparatus and methods for generating multispectral images that may be used for research, analysis, and/or diagnosis. In one embodiment, a digital colposcope may be used for imaging the cervix and for detecting pre-cancer. Such a colposcope advantageously allows for automated cancer screening and diagnosis of the cervix without undue reliance upon visualization skills of the operator.

Two-dimensional imaging of the cervix using techniques described herein will greatly improve optical diagnosis. Contextual classification techniques from images will increase diagnostic accuracy because information at one image location may be brought into context with neighboring information. Furthermore, two-dimensional data may be used to determine, for instance, the size of lesions and thus may be used to monitor development and spreading of pre-cancerous areas.

Figure 1:
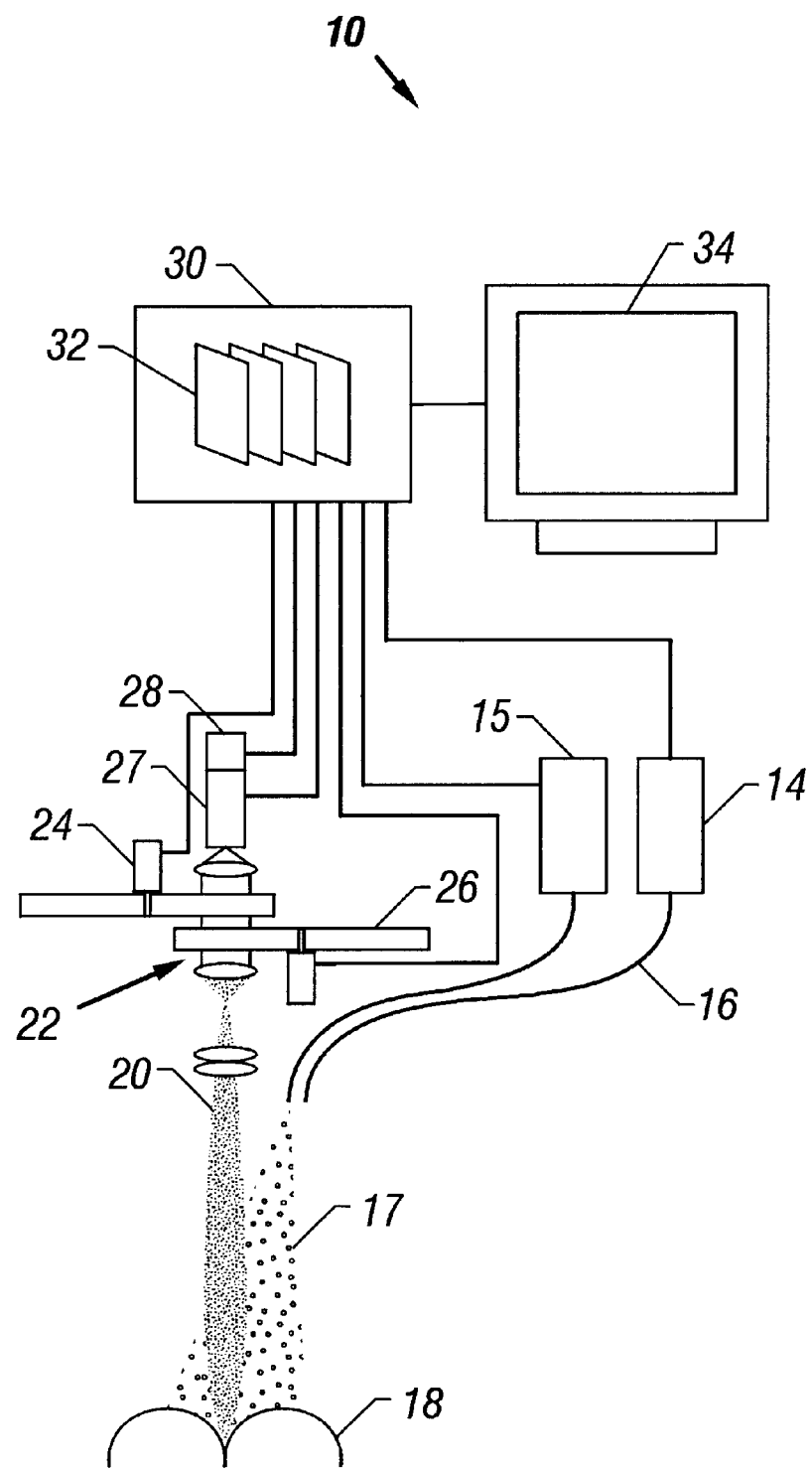
FIG. 1 shows a digital colposcope for fluorescence and reflectance imaging according to one embodiment of the present disclosure. In this embodiment, excitation light is produced with a Q-switched laser with a tunable OPO (Optical Parametric Oscillator). Fluorescence excited on the cervix is collimated and filtered through two 8 position filter wheels. Fluorescence is detected with an intensified gated camera.
Figure 2:
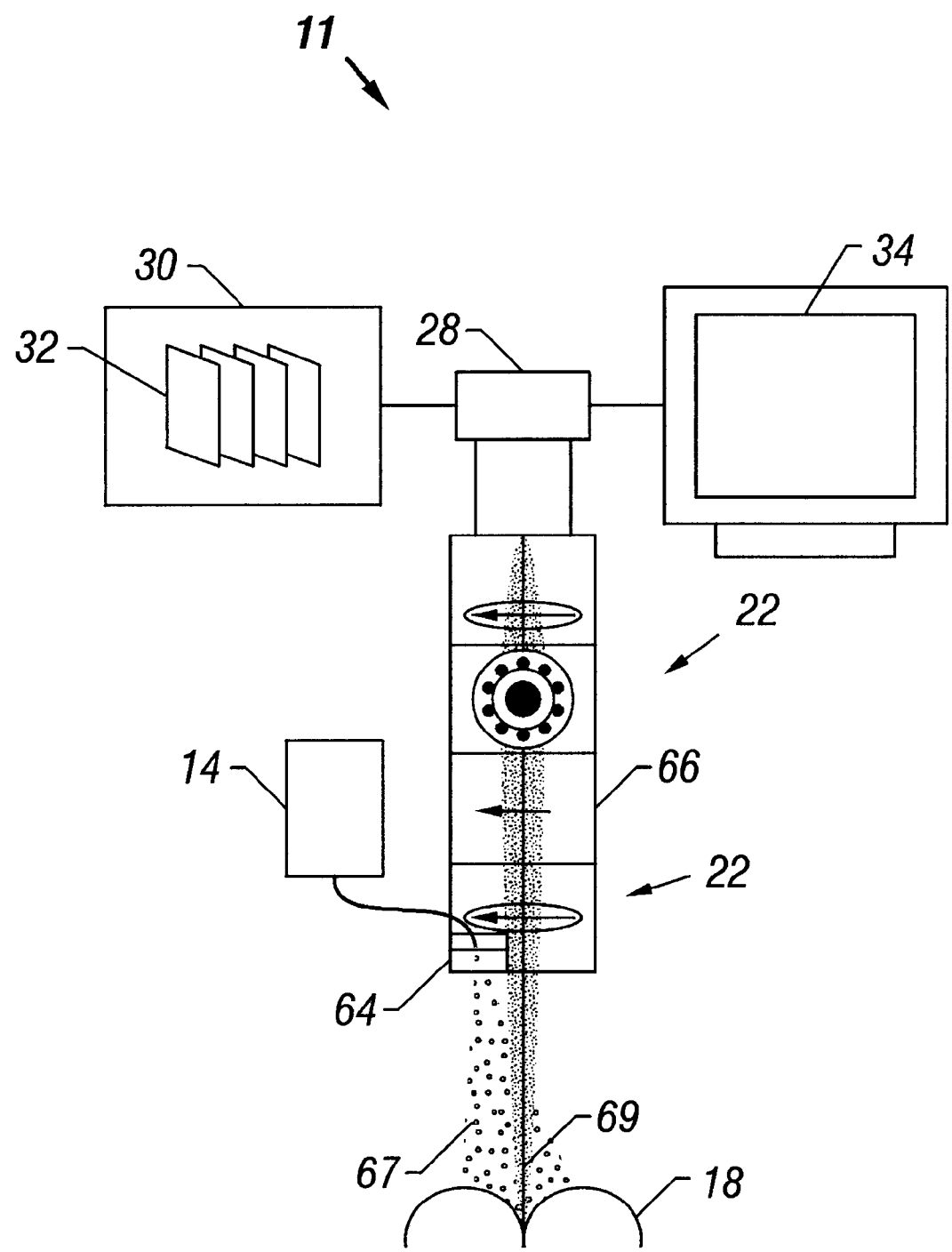
FIG. 2 shows a digital colposcope for polarized reflectance imaging according to one embodiment of the present disclosure. In this embodiment, light from a pulsed Xenon light source is linearly polarized and illuminated on to the cervix. Reflected light is collimated and passes a parallel and vertical polarization filter. Wavelength is selected with either a tunable filter or a mechanical filter wheel. Gated detection is made possible with an intensified CCD camera.
Figure 3:
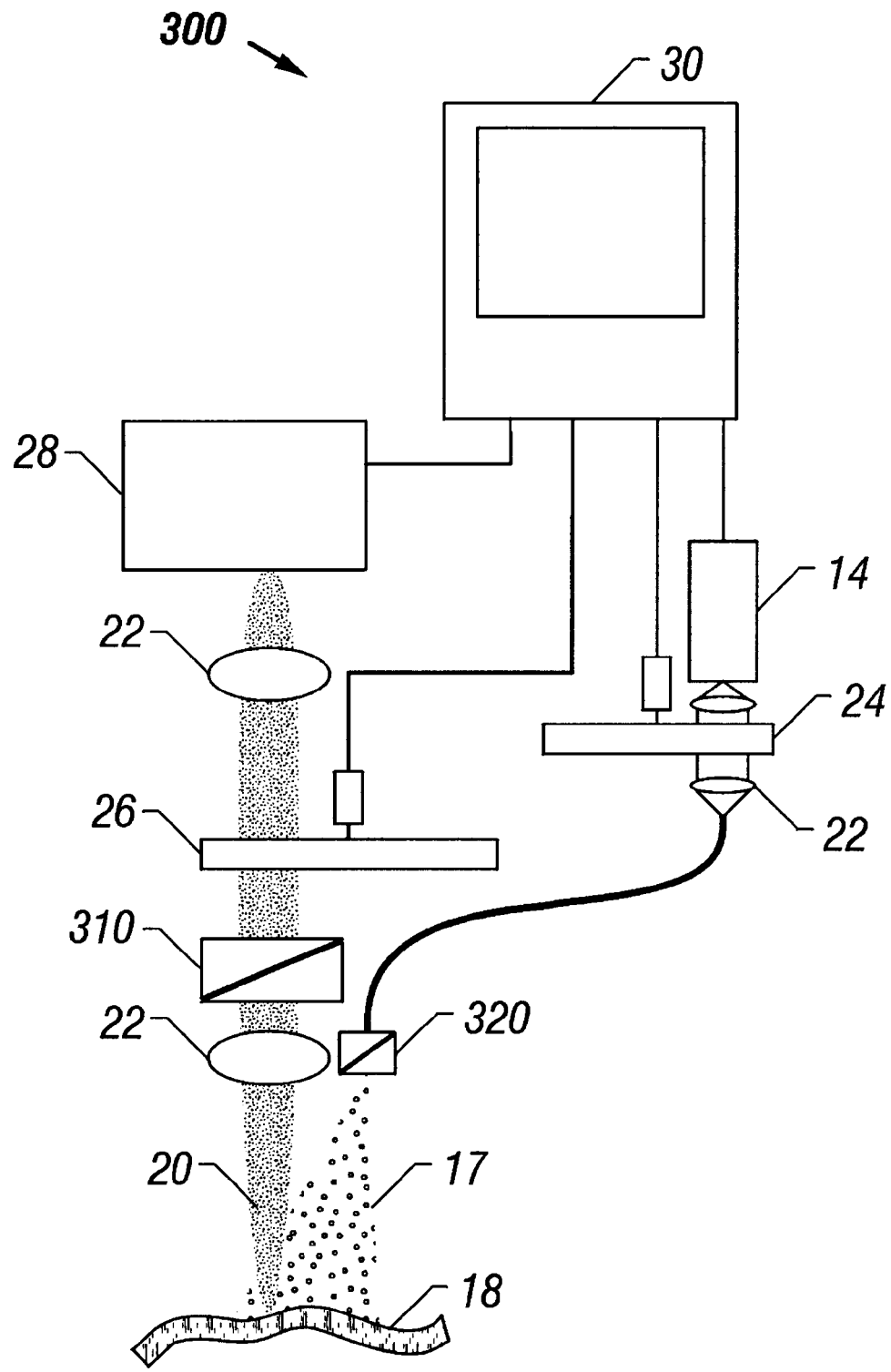
FIG. 3 shows a digital colposcope for polarized reflectance imaging according to one embodiment of the present disclosure. The main components include a light source, a detector, polarizer and filter wheels in front of the light source and detector, image optics, and computer.

FIGS. 1, 2, and 3 show digital colposcopes for imaging of the cervix according to embodiments of the present disclosure. This colposcope gathers a combination or a selection of fluorescence, reflectance, and/or polarized reflectance images. Apparatus 10 of FIG. 1 includes illumination sources 14 and 15, detector 28, detection filters 24 and 26, optics 22, analysis unit 30, and visualization unit 34. Apparatus 11 of FIG. 2 includes illumination source 14, illumination filter 64, detection filter 66, detector 28, optics 22, analysis unit 30, and visualization unit 34. Apparatus 300 of FIG. 3 includes illumination source 14, detector 28, detection filters 24 and 26, optics 22, polarizer 320, analysis unit 30, and polarizer-analyzer 310 (which collects light having a polarization parallel or perpendicular (or other orientation(s)) relative to the polarization of excitation, or illumination, light).

In operation, illumination sources 14 and 15 illuminate tissue 18 with radiation (see element 17 of FIGS. 1 and 3, element 67 of FIG. 2). In one embodiment, one or more illumination filters (not explicitly shown in FIG. 1) may be configured to select one or more wavelengths of illumination radiation and/or one or more polarizations of illumination radiation to be directed upon tissue 18. In one embodiment, such filters may be integral with illumination sources 14 and/or 15. For instance, if sources 14 and/or 15 are laser sources, those laser sources may be tuned as is known in the art to emit one or more different wavelengths. Likewise, those laser sources may be coupled to appropriate optical devices (integral or non-integral), as known in the art, to affect polarization characteristics.

In one embodiment, illumination source 15 may be a tunable pulsed laser for use as a fluorescence excitation source. Pulsed operation allows a gated detection technique that minimizes the influence of room light. The light source may be based on a Nd YAG laser with second and fourth harmonic frequency generation. However, with the benefit of the present disclosure, it will be apparent to those having skill in the art that several other laser sources may be suitable for use with the present invention. An optical parametric oscillator may be used to produce pulsed light adjustable from about 300 to 500 nm. The pulse may be chosen to have a repetition rate of about 10 Hz and an average of about 5 mJ per pulse. These parameters will allow simultaneous illumination of an entire cervix (about 3 cm in diameter) and detection of fluorescence in less than a second.

In one embodiment, fluorescence images may be acquired with ultraviolet-transmitting imaging optics, such as optics 20. Because a large working distance to the cervix may be required (greater than about 30 cm.), light may be collected with small-aperture objects. In such an embodiment, sensitive detectors are therefore mandatory. Fluorescence images may be obtained at up to 16 different emission wavelengths. Imaging bandpass filters mounted in a computer-controlled filter wheel (see, for example, elements 24 and 26 of FIGS. 1 and 3) may be used to select the desired emission wavelength ranges. In one embodiment, grated detection is made possible by an image intensifier 27, CCD camera 28 combination. Such a camera may be able to detect low-light images at about 5 frames per second.

In embodiments using reflectance measurements (see FIGS. 1, 2, and 3), the fluorescence light source may be replaced with a pulsed xenon flashlight (see illumination source 14 of FIGS. 1, 2, and 3). Pulse energies of a maximal 150 mJ with a repetition rate of about 300 Hz may be emitted over a spectral range of about 225–1100 nm. A custom-made (or commercially obtained) dielectric-coated mirror may be used to reflect a desired range of about 290–650 nm to minimize unnecessary ultraviolet and infrared radiation. Illumination source 14 (which may be about 1.2 inches in diameter) may be mounted onto a colposcope, and a collimating lens may alter the illumination angle to cover portions of, or an entire cervix. If the available space at the colposcope does not allow such integration, a flexible fiber bundle may be used to transport illumination (which may be filtered according to wavelength and/or polarization) to the colposcope. For polarized reflectance studies, the output of the collimator may be linearly polarized with a Glan polarizer, as is known in the art.

For polarized reflectance images the reflectance instrumentation may require the following additional changes. A polarization filter (see illumination filter 64 of FIG. 2, polarizer 320 of FIG. 3) may be used to select linear (or another orientation) polarized illumination light (50% transmission). A polarization filter with the same characteristics may be mounted in. a mechanical filter wheel, and one with perpendicular characteristics may be mounted in front of the detector 28, which may be an imaging camera. If more than 10 wavelengths need to be measured, a liquid-crystal tunable filter or the like may be used to measure spectrally resolved reflectance. Because many tunable filters are based on polarization techniques, cross-polarized light detection may require a variable retardation in front of the tunable filter. The retarder must be variable because the degree of retardation depends on the wavelength. A detector, such as a camera with a high dynamic range, may be necessary because the variation in the expected useful reflectance may be less than 2% of the total intensity.

In one embodiment, one or more detection filters, such as filters 24 and 26, may be placed in operative relation with detector 28. Detection filters 24 and 26 may be configured to select one or more wavelengths and/or one or more polarizations to pass to detector 28. As illustrated detector 28 may be positioned in operative relationship with an image intensifier. As illustrated, detection filters 24 and 26 may be electronically coupled via analysis unit 30 to illumination sources 14 and 15 (and any illumination filters associated therewith) so that the wavelengths and/or polarizations of the illumination and detection filters may be adjusted relative to one another to produce multispectral images. For instance, a first wavelength, $\lambda_1$, may be selected by an illumination filter, and a second wavelength, $\lambda_2$, may be selected by a detection filter in order to produce a $\lambda_1$, $\lambda_2$ multispectral image, as shown by 32 in FIG. 1.

In one embodiment, light reflected off a cervix (see element 20 of FIGS. 1 and 3, element 69 of FIG. 2) may be filtered with dielectric bandpass filters and then imaged with detector 28, which may be an intensified CCD camera. This camera may be equivalent to the detector used for fluorescence imaging. If the number of filters needed to obtain diagnostic information exceeds 16, a liquid-crystal tunable filter may be used instead of a mechanical filter wheel loaded with dielectric bandpass filters. In fact, any other type of filter suitable for filtering radiation may be used. For instance, in one embodiment, an accousto-optical filter may be used. As is known in the art, filters may be chosen with the wavelength ranges utilized in mind. For example, transmission through liquid tunable filters is limited in the UV to 380 nm., and protein absorption occurring at less than about 300 nm can only be measured with dielectric filters.

In one embodiment, analysis unit 30 may be configured not only to couple and/or control relative wavelength and polarization filters, but it may also be configured to generate a plurality of multispectral images 32 of tissue 18 according to different combinations of wavelength and/or polarization values. Analysis unit 30 may display the images as a composite image, incorporating one or more features of the images 32 into a single image. Images may be displayed on the visualization unit 34.

As noted via reference to fluorescence and reflectance imaging above, it will be apparent that the digital colposcope (and associated methodology) disclosed herein can be realized with a combination of several different, and varied, optical diagnostic techniques. The inventors have found that this combination of techniques further enhances diagnostic accuracy. For example, fluorescence may be sensitive to tissue metabolism while reflectance may be sensitive to tissue structure. Polarization may be used to select single or minimal backscattered light. Pre-cancerous and cancerous changes (and many other tissue conditions) may affect any one, any combination, or all of these optical properties. Noting those changes allows for successful diagnostic analysis.

As already mentioned, apparatus and methodology disclosed herein may use fluorescence imaging. Fluorescence imaging, the principles of which are well known in the art, has been successfully used as a diagnostic tool in the lung and the bladder and has also been proposed for the skin.

Additionally, reflectance imaging, the principles of which are well known in the art, may also be used with the apparatus and methodology disclosed herein. Reflectance imaging of the cervix with the colposcope is a standard diagnostic procedure. Spectral filtering enhances the visualization of abnormal areas. Increased spectral resolution may target the absorption peaks of oxygenated (415, 545, and 577 mm) and deoxygenated hemoglobin (430, and 555 mm). As with pulse oximetry, tissue oxygenation may be calculated by measuring reflectance at wavelengths around the isobestic points (568 and 587 nm). Accuracy may be increased by modeling scattering and absorption with data from further wavelengths.

Polarized reflectance images may include light scattered only from the upper 300 $\mu$m of cervical tissue, which is where neoplastic changes occur. As is known in the art, polarization techniques may be used to extract light from these layers. The light originating in the uppermost tissue layer may be backscattered with a minimal amount of scattering events and therefore maintains its polarization. This light may be about 5% of the total reflected light. When the tissue is illuminated with polarized light, subtracting the difference in the parallel polarized filtered image and the perpendicular polarized filtered image removes about 90% of light originating from deeper tissue layers. Normalization by an image, that is the sum of the parallel and perpendicular filtered images cancels common attenuation. Specular reflected light may be canceled out with a camera slightly tilted with respect to the surface. Because the cervix is curved, at least two measurements from different angles may need to be taken.

Nuclear size, which may then be correlated with several different tissue classifications, may be measured using the teachings of the present disclosure. In particular, nuclear size may be measured based on the reflectance spectra of fine-structures. These fine-structures measurements may be extracted from the reflectance signal by removing mathematically modeled components of diffuse scattering and absorption. The nuclear size distribution may be calculated with a Fourier transformation of the spectral range of about 400–700 nm as is known in the art. Good spectral resolution and a signal-to-noise ratio of more than 100 may be necessary for this technique.

In one embodiment, polarization filtration may be combined with Mie scattering theory to obtain nuclear size distribution without the need for complex physical modeling of the measured data, as described in Provisional Patent Application No. 60/192,540, entitled, "Methods and Apparatus for Polarized Reflectance Spectroscopy," filed on Mar. 28, 2000, which is hereby incorporated by reference in its entirety.

All of the methods, systems, and apparatus disclosed and claimed herein can be made and executed without undue experimentation in light of the present disclosure. While the techniques of this invention have been described in terms of specific embodiments, it will be apparent to those of skill in the art that many variations may be applied to the disclosed methodologies and in the steps of the methods described herein without in any way departing from the concept, spirit and scope of the invention.

EXAMPLE 1

In vivo measurements of fluorescence excitation-emission matrices (EEMs) were performed and the resultant data was analyzed to determine the optimal excitation wavelengths for diagnosis of cervical neoplasia, and to estimate the sensitivity and specificity at this combination of excitation wavelengths.

1. Materials

Eligible patients included those over the age of 18 who were not pregnant, who were referred with an abnormal Pap smear. All patients underwent a demographic interview, risk factor questionnaire, complete history and physical exam and pan-colposcopy of the vulva, vagina and cervix. Initially, each patient underwent a urine pregnancy test, chlamydia and ghonorrhea cultures, and a Papanicoloau smear. Additionally, patients underwent Virapap testing (DiGene, Bethesda, Md.) as well as HPV DNA and mRNA sampling. Each patient had blood drawn for FSH, Estradiol, and Progesterone levels. The last menstrual period and menstrual history were asked of each patient.

During colposcopy, two colposcopically normal sites and one colposcopically abnormal site were chosen by the physician or nurse colposcopists and fluorescence EEMs were measured from these three sites. It was noted whether these sites corresponded to squamous or columnar epithelium or the transformation zone.

Following fluorescence measurement, each site was biopsied and submitted for histopathologic diagnosis. Each Papanicolau smear was read by the clinician assigned to the case that day, and was subsequently reviewed by the study cytologist. Discrepant cases were reviewed a third time for consensus diagnosis by the study cytologist. Each biopsy was read by the clinician assigned to the case that day, and was subsequently reviewed by the study histopathologist. Again, discrepant cases were reviewed a third time for consensus diagnosis by the study histopathologist. Standard diagnostic criteria were used and consensus diagnostic categories included: normal squamous epithelium, normal columnar epithelium, low grade squamous intraepithelial lesion (LGSIL), high grade squamous intraepithelial lesion (HGSIL) and invasive cancer.

2. Instrumentation

One embodiment of the apparatus of the present invention was used to measure fluorescence excitation-emission matrices (EEMs). The apparatus measured fluorescence emission spectra at 16 excitation wavelengths, ranging from 330 nm to 480 nm in 10 nm increments with a spectral resolution of 7 nm. The apparatus incorporated a fiberoptic probe, a Xenon arc lamp coupled to a monochromator to provide excitation light and a polychromator and thermo-electrically cooled CCD camera to record fluorescence intensity as a function of emission wavelength.

3. Measurements

As a negative control, a background EEM was obtained with the probe immersed in a non-fluorescent bottle filled with distilled water at the beginning of each day. Then a fluorescence EEM was measured with the probe placed on the surface of a quartz cuvette containing a solution of Rhodamine 610 (Exciton, Dayton, Ohio) dissolved in ethylene glycol (2 mg/mL) at the beginning of each patient measurement.

To correct for the non-uniform spectral response of the detection system, the spectra of two calibrated sources were measured at the beginning of the study. In the visible, an NIST traceable calibrated tungsten ribbon filament lamp was used, and in the UV a deuterium lamp was used (550C and 45D, Optronic Laboratories Inc, Orlando, Fla.). Correction factors were derived from these spectra. Dark current subtracted EEMs from patients were then corrected for the non-uniform spectral response of the detection system.

Variations in the intensity of the fluorescence excitation light source at different excitation wavelengths were corrected using measurements of the intensity at each excitation wavelength at the probe tip made using a calibrated photodiode (818-UV, Newport Research Corp.). Finally, corrected fluorescence intensities from each site were divided by the fluorescence emission intensity of the Rhodamine standard at 460 nm excitation, 580 nm emission. Thus, the included data is not the absolute fluorescence intensities of tissue but rather is given in calibrated intensity units relative to the Rhodamine standard.

Before the probe was used it was disinfected with Metricide (Metrex Research Corp.) for 20 minutes. The probe was then rinsed with water and dried with sterile gauze. The disinfected probe was guided into the vagina and its tip positioned flush with the cervical epithelium. Then fluorescence EEMs were measured from three cervical sites. Measurement of each EEM required approximately two minutes.

4. Data Analysis

All spectra were reviewed by two investigators blinded to the pathologic results. Spectra were discarded if files were not saved properly due to software error, instrument error, operator error, probe movement, and the presence of room light artifacts at wavelengths below 600 nm in at least one of the emission spectra.

Fluorescence data were analyzed to determine which excitation wavelengths contained the most diagnostically useful information and to estimate the performance of diagnostic algorithms based on this information. Algorithms based on multi-variate discriminant analysis were considered. First, algorithms were developed based on combinations of emission spectra at various excitation wavelengths in order to determine which excitation wavelengths contained the most diagnostic information.

In each case, the algorithm development process, described in detail below, consisted of the following major steps: (1) data pre-processing to reduce inter-patient variations, (2) data reduction to reduce the dimensionality of the data set, (3) feature selection and classification to develop algorithms which maximized diagnostic performance and minimized the likelihood of over-training in a training set, (4) evaluation of these algorithms using the technique of cross-validation.

Multi-variate discriminant algorithms were sought to separate two histologic tissue categories: normal and neoplastic. The neoplastic class contained sites with LGSIL, HGSIL or cancer; the normal class contained sites which were histologically normal, had squamous metaplasia or chronic and acute inflammation.

Fluorescence data from a single measurement site is represented as a matrix containing calibrated fluorescence intensity as a function of excitation and emission wavelength. Columns of this matrix correspond to emission spectra at a particular excitation wavelength; rows of this matrix correspond to excitation spectra at a particular emission wavelength. Each excitation spectrum contains 18 intensity measurements; each emission spectrum contains between 50 and 130 intensity measurements depending on excitation wavelength. Finally, emission spectra were truncated at 600 nm emission to eliminate the highly variable background due to room light present above 600 nm. Most multi-variate data analysis techniques require vector input, so the column vectors containing the emission spectra at excitation wavelengths selected for evaluation were concatenated into a single vector.

Previous studies have illustrated that spectra of the cervix obtained in vivo show large patient to patient variations in intensity that can be greater than the inter-category differences. Therefore, pre-processing methods to reduce the inter-patient variations, while preserving inter-category differences, were explored. Two methods were selected for evaluation: (1) normalization of all emission spectra in a concatenated vector by the largest emission intensity contained within that vector, and (2) normalization of each emission spectra to its maximum intensity.

In this example, fluorescence emission spectra were measured at 18 different excitation wavelengths. A goal of the data analysis was to determine which combination of excitation wavelengths contained the most diagnostic information. Combinations of emission spectra from up to four excitation wavelengths were considered. Limiting the device to four wavelengths allows for construction of a reasonably cost-effective clinical spectroscopy system. To identify the optimal combination of excitation wavelengths, all possible combinations of up to four wavelengths chosen from the 18 possible excitation wavelengths were evaluated. This equated to 18 combinations of one, 153 combinations of two, 816 combinations of three, and 3,060 combinations of four excitation wavelengths, for a total of 4,047 combinations.

For each of the 4,047 combinations of one to four excitation wavelengths, multi-variate algorithms were developed to separate normal and abnormal tissues based on their fluorescence emission spectra at all possible wavelength combinations. Algorithm development consisted of three steps: (1) pre-processing, (2) data reduction and (3) development of a classification algorithm which maximized diagnostic performance.

Data were pre-processed using the two normalization schemes described above. For each normalization, principal component analysis was performed using the entire dataset and eigenvectors accounting for 65, 75, 85, and 95% of the total variance were retained. Principal component scores associated with these eigenvectors were calculated for each sample. Discriminant functions were then formed to classify each sample as normal or abnormal. The classification was based on the Mahalanobis distance, which is a multivariate measure of the separation of a point from the mean of a dataset in n-dimensional space. The sample was classified to the group from which it was the shorter Mahalonobis distance. The sensitivity and specificity of the algorithm were then evaluated relative to diagnoses based on histopathology.

Overall diagnostic performance was evaluated as the sum of the sensitivity and the specificity, thus minimizing the number of misclassifications (when prevalence of disease and normal are approximately equal). The performance of the diagnostic algorithm depended on the principal component scores which were included. Four different diagnostic algorithms were developed using principal component scores derived from eigenvectors accounting for increasing amounts of total variance. From the available pool of principle component scores, the single principal component score yielding the best initial performance was identified, and then the principal component score that most improved this performance was selected. This process was repeated until performance is no longer improved by the addition of principal components scores, or all available scores were selected.

The pool of available eigenvectors is specified by a variance criterion, eigenvector significance level (ESL) that represents the minimum variance fraction accounted for by the sum of the n largest eigenvalues. In this work we examined 4 ESLs, corresponding to 65%, 75%, 85% and 95% of the total variance.

At each ESL, algorithm performance was noted for each wavelength combination, using the sum of sensitivity and specificity as a metric of performance. The 25 combinations of excitation wavelengths with the highest performance were then identified. However, as the ESL approaches 100%, over-training becomes more likely, since the available pool of eigenvectors will account for nearly 100% of the variance, including variance due to noise. The magnitude of diagnostically important variances is unknown. The risk of over-training was assessed at the top 25 wavelength combinations of two, three, and four excitation wavelengths, by performing cross-validation to yield an unbiased estimate of algorithm performance.

This experiment revealed that the results of the top 25 wavelengths appear to be in the following ranges:

(a) For two wavelength combinations (w/Eigenvector = 0.65):
first wavelength range is between about 330 nm and about 360 nm
second wavelength range is between about 390 nm and about 440 nm
(b) For two wavelength combinations (w/Eigenvector = 0.95):
first wavelength range is between about 340 nm and about 360 nm
second wavelength range is between about 420 nm and about 460 nm
(c) For three wavelength combinations (w/Eigenvector = 0.65):
first wavelength range is between about 340 nm and about 350 nm
second wavelength range is between about 370 nm and about 390 nm
third wavelength range is between about 420 nm and about 430 nm or between about 460 nm and about 470
(d) For three wavelength combinations (w/Eigenvector 0.95):
first wavelength range is between about 340 nm and about 350 nm
second wavelength range is between about 360 nm and about 380 nm
third wavelength range is between about 450 nm and about 480 nm
(e) For four wavelength combinations (w/Eigenvector = 0.65):
first wavelength range is between about 340 nm and about 350 nm
second wavelength range is between about 370 nm and about 390 nm
third wavelength range is between about 420 nm and about 440 nm
fourth wavelength range is between about 460 nm and about 480 nm

EXAMPLE 2

Epithelial neoplastic changes occur in the upper layers of epithelial tissue. For imaging of pre-cancers, it is important to collect optical signals originated from these layers of epithelium. When tissue is illuminated with polarized light, the portion of the light which is scattered back to a detector from the uppermost tissue layers undergoes a minimal amount of scattering events and therefore maintains the original polarization. In some instances, this may also be the case for fluorescently emitted light.

The light that penetrates deeper in the tissue is scattered back after multiple scattering events and is depolarized. The component of light collected with polarization parallel relative to the polarization of illumination consists of the signal originating from the upper epithelial layer and half of the signal from the deeper layers of epithelium. The perpendicular component contains the another half of the multiple scattered light. The following procedure may be used for selective imaging of the upper epithelial layer.

First, a contrast agent may be applied and the excess washed out. Next, an organ site may be illuminated with polarized light and optical images may be collected with analyzing polarizer in parallel and perpendicular positions relative to the polarization of the excitation light. The image obtained in perpendicular configuration may be subtracted from the image obtained in parallel configuration. This procedure will remove multiple scattered light originating from the deeper stromal layer of epithelial tissue and will preserve the light collected from the upper epithelial layer.

In the case of fluorescence, the quality of imaging may be increased due to two major factors. First, the autofluorescence of stomal layer may be removed. Second, about a half of the fluorescent photons emitted by the labeled probes will enter tissue, diffuse inside at the distances in the order of millimeters, and, then, backscatter to the surface of the tissue. These photons may also be eliminated from the polarization filtered image. This will increase the sharpness of the image and eliminate the influence of blood absorption on the intensity of fluorescence. In the case of reflectance imaging, both the hemoglobin absorption and the diffuse background scattering will be dramatically reduced. These improvements of the polarized imaging provide the possibility of accurate quantitative analysis of molecular specific biomarkers for pre-cancer detection and grading.

The proposed approaches may also be tested on human biopsies and excised specimens from human body as a result of a surgical procedure.

REFERENCES

The following references, to the extent that they provide exemplary procedural or other details supplementary to those set forth herein, are specifically incorporated herein by reference.

1. Lam S. MacAulay C. Paleic B. Detection and localization of early lung cancer by imaging techniques. [Review] [40 refs] Chest 103 (1 Suppl): 12S–14S, 1993 January.
2. Jichlinski P. Forrer M. Mizeret J. Glanzmann T. Braichotte D. Wagnieres G. Zimmer G. Guillou L. Schmidlin F. Graber P. van den Bergh H. Leisinger H J., Clinical evaluation of a method for detecting superficial surgical transitional cell carcinoma of the bladder by light-induced fluorescence of protoporphyrin IX following the topical application of S-aminolevulinic acid: preliminary results, Lasers in Surgery & Medicine. 20(4):402–8, 1997.
3. Sterenborg, N J. Thomsen S. Jacques S L. Duvic M. Motamedi M. Wagner R F Jr. In vivo fluorescence spectroscopy and imaging of human skin tumors [letter]. Dermatologic Surgery. 21(9):821–2, 1995 September.
4. Svanberg K. Wang I. Colleen S. Idvall I. Ingvar C. Rydell R. Jocham D. Diddens H. Bown S. Gregory G. Montan S. Andersson-Engels S. Svanberg S. Clinical multi-colour fluorescence imaging of malignant tumours-initial experience. Acta Radiologica 39(1):2–9, 1998 January.
5. Pogue B W, Burke G C, Weave J. Harper D M; Development of Spectrally-Resolved Colposcopc for Early Detection of Cervical Cancer in Biomedical Optical Spectroscopy and Diagnostic, Technical Digest (Optical Society of America, Washington, DC, 1998), pp.87–89.
6. [http://ee.ogi.edu/omlc/news/feb98/polarization/index.html]
7. L. T. Perelman, V. Backman, M. Wallace, G. Zonios, R. Manoharan, A. Nusrat, S. Shields, M. Seiler. C. Lima, T. Hamano, I. Itzkan. J. Van Dam. J. M. Crawford, M. S. Feld, Observation of Periodic Fine Structure in Reflectance from Biological Tissue: A New Technique for Measuring Nuclear Size Distribution. Physical Review Letters, 80(3), January 1998.
8. U.S. Pat. No. 5,590,660, Jan. 7.1997.
9. U.S. Pat. No. 5,647,368, Jul. 15, 1997.

10. U.S. patent application Ser. No. 08/632,018.
11. U.S. Pat. No. 5,421,339.

What is claimed is:

1. An apparatus for generating multispectral images of tissue, comprising:
   an illumination source configured to illuminate the tissue with radiation;
   a detector configured to collect radiation from the tissue;
   an illumination filter in operative relation with the illumination source, the illumination filter configured to select a first wavelength and a first polarization of radiation to be directed from the source to the tissue;
   a detection filter in operative relation with the detector, the detection filter configured to select a second wavelength and a second polarization of radiation to be directed from the tissue to the detector; and
   an analysis unit in operative relation with the detector, the analysis unit configured to generate a plurality of multispectral images of the tissue according to different combinations of first and second wavelengths and first and second polarizations;
   wherein the plurality of multispectral images comprise images of fluorescence, reflectance, polarized reflectance, or any combination thereof.

2. The apparatus of claim 1, wherein the first and second wavelengths are equal.

3. The apparatus of claim 1, wherein the first and second polarizations are equal.

4. The apparatus of claim 1, further comprising:
   illumination optics in operative relation with the illumination source, the illumination optics configured to direct radiation from the illumination source to the tissue; and
   imaging optics in operative relation with the tissue, the imaging optics configured to direct radiation from the tissue to the detector.

5. The apparatus of claim 4, wherein the illumination optics comprises a fiber bundle.

6. The apparatus of claim 4, wherein the detection optics comprises a fiber bundle.

7. The apparatus of claim 1, wherein the illumination filter is integral with the illumination source.

8. The apparatus of claim 1, wherein the detection filter is integral with the detector.

9. The apparatus of claim 1, wherein the illumination source comprises a tunable pulsed laser.

10. The apparatus of claim 1, wherein the illumination source comprises a pulsed flashlight.

11. The apparatus of claim 1, wherein the detector comprises a CCD camera.

12. The apparatus of claim 1, wherein the illumination filter comprises a bandpass filter, a filter wheel, or a tunable filter.

13. The apparatus of claim 12, wherein the tunable filter comprises an acousto-optical filter or a liquid crystal filter.

14. The apparatus of claim 1, wherein the detection filter comprises a bandpass filter, a filter wheel, or a tunable filter.

15. The apparatus of claim 14, wherein the tunable filter comprises an acousto-optical filter or a liquid crystal filter.

16. The apparatus of claim 1, wherein the illumination and detection filters are integral.

17. The apparatus of claim 1, wherein the tissue comprises a cervix.

18. The apparatus of claim 1, wherein the plurality of multispectral images comprise images of approximately the entire cervix.

19. The apparatus of claim 1, wherein the apparatus is coupled to an endoscope.

20. The apparatus of claim 1, wherein the apparatus is coupled to a colposcope.

21. The apparatus of claim 1, wherein the analysis unit is further configured to generate a composite image of the tissue, the composite image incorporating one or more features of the plurality of multispectral images.

22. The apparatus of claim 21, wherein the composite image comprises information relating to the size of one or more lesions of the tissue.

23. A method for generating multispectral images of tissue, comprising:
   producing primary radiation with an illumination source;
   filtering the primary radiation to select a first wavelength and a first polarization;
   illuminating the tissue with the filtered primary radiation to generate secondary radiation;
   filtering the secondary radiation to select a second wavelength and a second polarization;
   collecting the filtered secondary radiation with a detector; and
   generating a plurality of multispectral images of the tissue according to different combinations of first and second wavelengths and first and second polarization with an analysis unit in operable relation with the detector;
   wherein the plurality of multispectral images comprise images of fluorescence, reflectance, polarized reflectance, or any combination thereof.

24. The method of claim 23, further comprising generating a composite image of the tissue, the composite image incorporating one or more features of the plurality of multispectral images.

25. The method of claim 24, further comprising determining the size of one or more lesions using the composite image.

* * * * *

UNITED STATES PATENT AND TRADEMARK OFFICE
CERTIFICATE OF CORRECTION

PA,TENT NO. : 6,766,184 B2 Page 1 of 1
DATED : July 20, 2004
INVENTOR(S) : Utzinger et al.

It is certified that error appears in the above-identified patent and that said Letters Patent is hereby corrected as shown below:

Title page,
Item [75], Inventors, delete "MacAuldy" and insert -- MacAulay --; and delete "Cancouver" and insert -- Vancouver --.

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,766,184 B2  Page 1 of 1
APPLICATION NO. : 09/821786
DATED : July 20, 2004
INVENTOR(S) : Urs Utzinger et al.

It is certified that error appears in the above-identified patent and that said Letters Patent is hereby corrected as shown below:

In column 1, line 12, insert
--This invention was made with government support under grant number CA072650 awarded by the National Institutes of Health. The government has certain rights in the invention.--.

Signed and Sealed this

Twenty-second Day of December, 2009

David J. Kappos
*Director of the United States Patent and Trademark Office*